(12) United States Patent
Onishi et al.

(10) Patent No.: US 8,267,102 B2
(45) Date of Patent: Sep. 18, 2012

(54) WASHING TUBE AND ENDOSCOPE WASHING AND DISINFECTING APPARATUS

(75) Inventors: Hideto Onishi, Tokyo (JP); Eiri Suzuki, Kanagawa (JP); Masahiko Tomita, Tokyo (JP); Toshiaki Noguchi, Tokyo (JP); Ryuta Sewake, Tokyo (JP); Hitoshi Hasegawa, Hamburg (DE)

(73) Assignee: Olympus Medical Systems Corp., Tokyo (JP)

( * ) Notice: Subject to any disclaimer, the term of this patent is extended or adjusted under 35 U.S.C. 154(b) by 783 days.

(21) Appl. No.: 12/355,036

(22) Filed: Jan. 16, 2009

(65) Prior Publication Data

US 2009/0205687 A1    Aug. 20, 2009

(30) Foreign Application Priority Data

Feb. 20, 2008   (JP) ................. 2008-039028

(51) Int. Cl.
*B08B 9/032*    (2006.01)
(52) U.S. Cl. ........................... 134/170; 134/136
(58) Field of Classification Search .............. 422/28; 134/22.11, 66 C, 167 C, 168 C1, 166 C, 168 C, 134/170

See application file for complete search history.

(56) References Cited

U.S. PATENT DOCUMENTS 6,041,794 A * 3/2000 Lin et al. .............. 134/22.11
6,354,312 B1   3/2002 Lin et al.

FOREIGN PATENT DOCUMENTS

| GB | 383633   | 11/1932 |
|----|----------|---------|
| JP | 06-098857 | 4/1994  |
| JP | 11-099121 | 4/1999  |

* cited by examiner

*Primary Examiner* — Michael Barr
*Assistant Examiner* — Caitlin N Dunlap
(74) *Attorney, Agent, or Firm* — Scully, Scott, Murphy & Presser, P.C.

(57) ABSTRACT

A washing tube of the present invention is a washing tube for supplying a washing and disinfecting fluid to an endoscope conduit of an endoscope placed in an endoscope washing and disinfecting apparatus, includes: a tube body, one end of which is connected to fluid supply sections of the endoscope washing and disinfecting apparatus for sending a fluid, a connector section disposed at the other end of the tube body and loosely and detachably fitted to a base of the endoscope conduit, a sealing member that is provided inside the connector section and comes into close contact with the base to keep the base and the connector section connected in a watertight manner, a valve body that moves forward by a liquid sending pressure of the supplied fluid and a biasing member provided inside the connector section for biasing the valve body backward.

3 Claims, 11 Drawing Sheets

WASHING TUBE AND ENDOSCOPE WASHING AND DISINFECTING APPARATUS

This application claims benefit of Japanese Application No. 2008-039028 filed in Japan on Feb. 20, 2008, the contents of which are incorporated herein by this reference.

BACKGROUND OF THE INVENTION

1. Field of the Invention

The present invention relates to an endoscope washing and disinfecting apparatus that automatically washes and disinfects an endoscope and a washing tube used for the endoscope washing and disinfecting apparatus.

2. Description of the Related Art

Endoscopes are widely used in the medical and industrial fields in recent years. By inserting an elongated insertion portion of an endoscope used in the medical field into a body cavity, it is possible to observe organs in the body cavity and give, if necessary, treatment using a treatment instrument inserted into a treatment instrument insertion channel provided for the endoscope.

Since endoscopes in the medical field are used to be inserted into the body cavity especially for the purposes of inspection and medical treatment, the endoscopes need to be washed and disinfected after use so as to be reused. It is known that such used endoscopes are washed and disinfected using endoscope washing apparatuses disclosed, for example, in Japanese Patent Application Laid-Open Publication No. 6-98857 and Japanese Patent Application Laid-Open Publication No. 11-99121. Furthermore, an endoscope is provided with a plurality of channels and not only the outer surface of the endoscope but also the inside of the channels need to be washed.

The endoscope washing apparatus disclosed in Japanese Patent Application Laid-Open Publication No. 6-98857 is of a type that a washing tube for sending washing water into a channel is manually fitted to a connector which is a channel base. A tube connector section of the conventional washing tube is provided with a clearance and letting washing water leak from this clearance allows the outer surface of the connector which is the channel base to be also washed.

Furthermore, the endoscope washing apparatus disclosed in Japanese Patent Application Laid-Open Publication No. 11-99121 provides a washing fluid supply nozzle that sends washing water into a channel with an attaching/detaching mechanism that allows detachment from a connector which is a channel base so that a part contacting the contaminated connector can also be washed.

SUMMARY OF THE INVENTION

A washing tube according to the present invention is a washing tube for supplying a washing and disinfecting fluid to an endoscope conduit of an endoscope placed in an endoscope washing and disinfecting apparatus, includes: a tube body, one end of which is connected to a fluid supply section of the endoscope washing and disinfecting apparatus, for sending the fluid, a connector section disposed at the other end of the tube body and loosely fitted into a base of the endoscope conduit in a detachable manner, a sealing member provided inside the connector section that comes into close contact with the base for keeping the base and the connector section connected watertight, a valve body that moves forward by a liquid sending pressure of the supplied fluid and a biasing member provided inside the connector section for biasing the valve body backward.

Furthermore, the endoscope washing and disinfecting apparatus according to the present invention is an endoscope washing and disinfecting apparatus that automatically washes and disinfects an endoscope placed in a washing and disinfecting tank and detects conduit clogging of an endoscope conduit of the endoscope, includes: a tube body, one end of which is connected to a fluid supply section for sending the fluid, a connector section disposed at the other end of the tube body and loosely fitted into a base of the endoscope conduit in a detachable manner, a sealing member provided inside the connector section that comes into close contact with the base for keeping the base and the connector section connected watertight, a valve body that moves forward by a liquid sending pressure of the fluid, and a biasing member provided inside the connector section for biasing the valve body backward, wherein the valve body supplies a predetermined flow rate of the fluid from the fluid supply section to the connector section via the tube body against a biasing force of the biasing member so as to produce a predetermined liquid sending pressure so that the sealing member comes into close contact with the base and moves forward up to a position where the sealing member keeps the base and the connector section connected watertight.

The above and other objects, features and advantages of the invention will become more clearly understood from the following description referring to the accompanying drawings.

DETAILED DESCRIPTION OF THE PREFERRED EMBODIMENTS

Hereinafter, the present invention will be explained with reference to the accompanying drawings.

First Embodiment

First, a first embodiment of the present invention will be explained based on FIG. 1 to FIG. 10.

Figure 1:
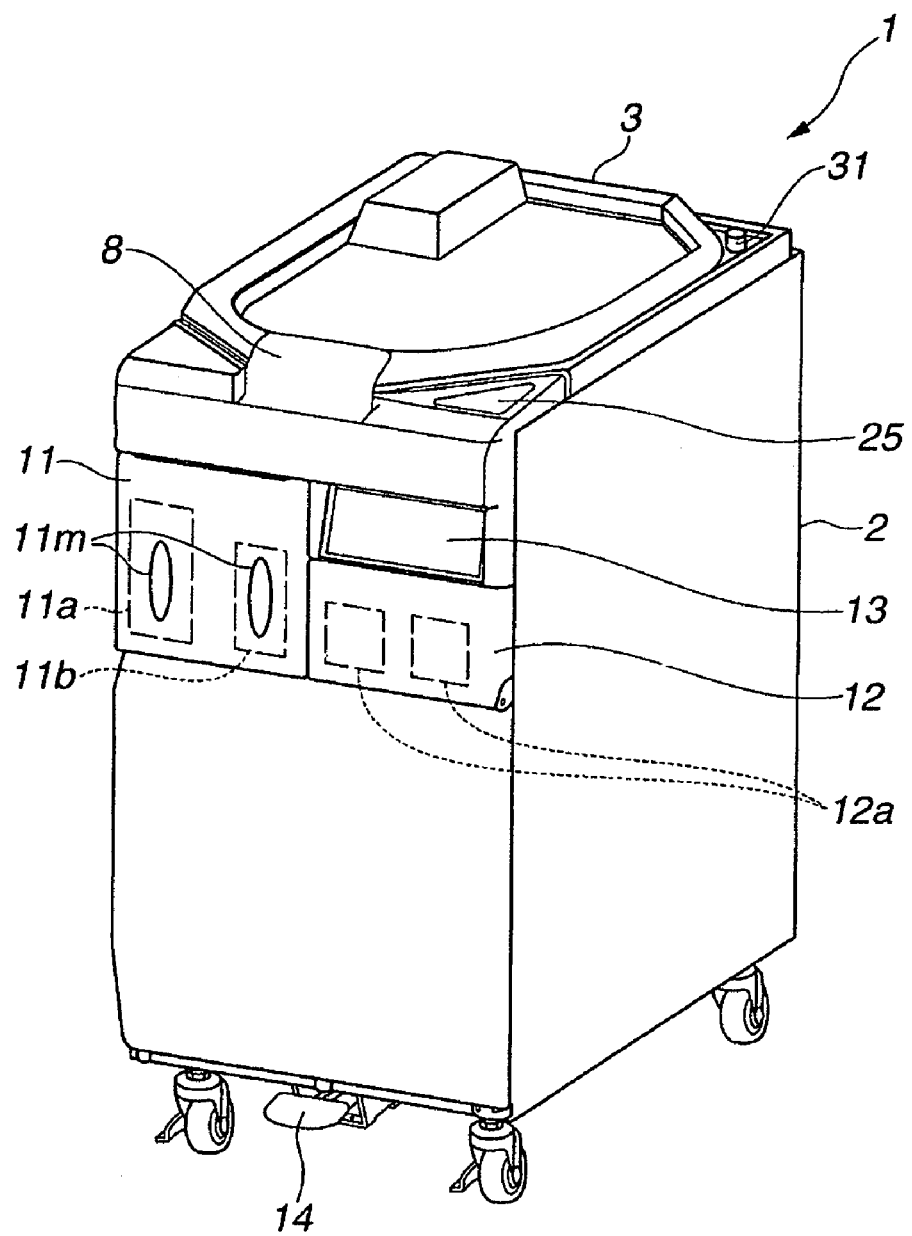
FIG. 1 is a perspective view of an endoscope washing and disinfecting apparatus according to a first embodiment.
Figure 2:
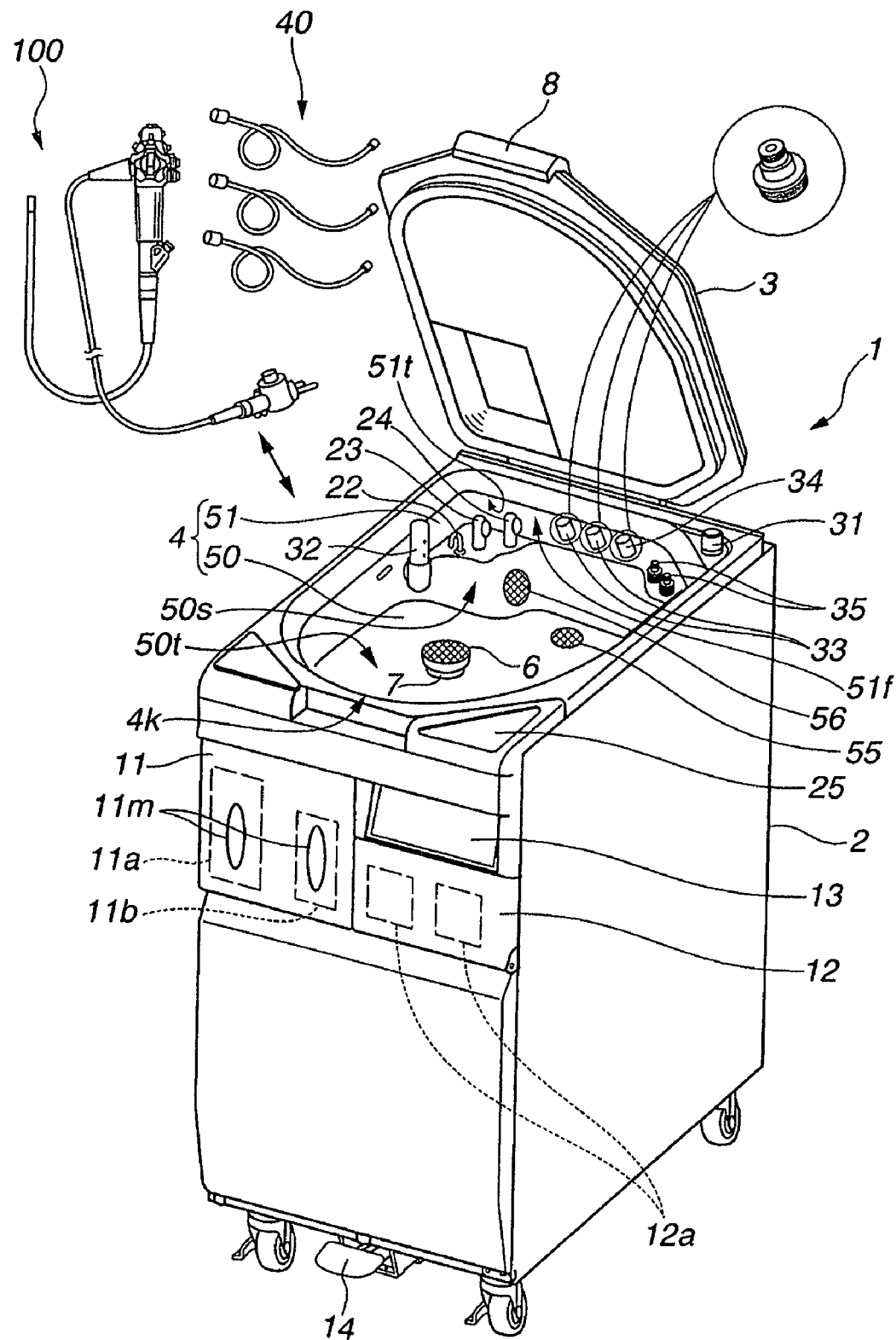
FIG. 2 is a perspective view of the endoscope washing and disinfecting apparatus according to the first embodiment with the top cover in FIG. 1 left open so as to freely accommodate the endoscope in the washing and disinfecting tank.
Figure 3:
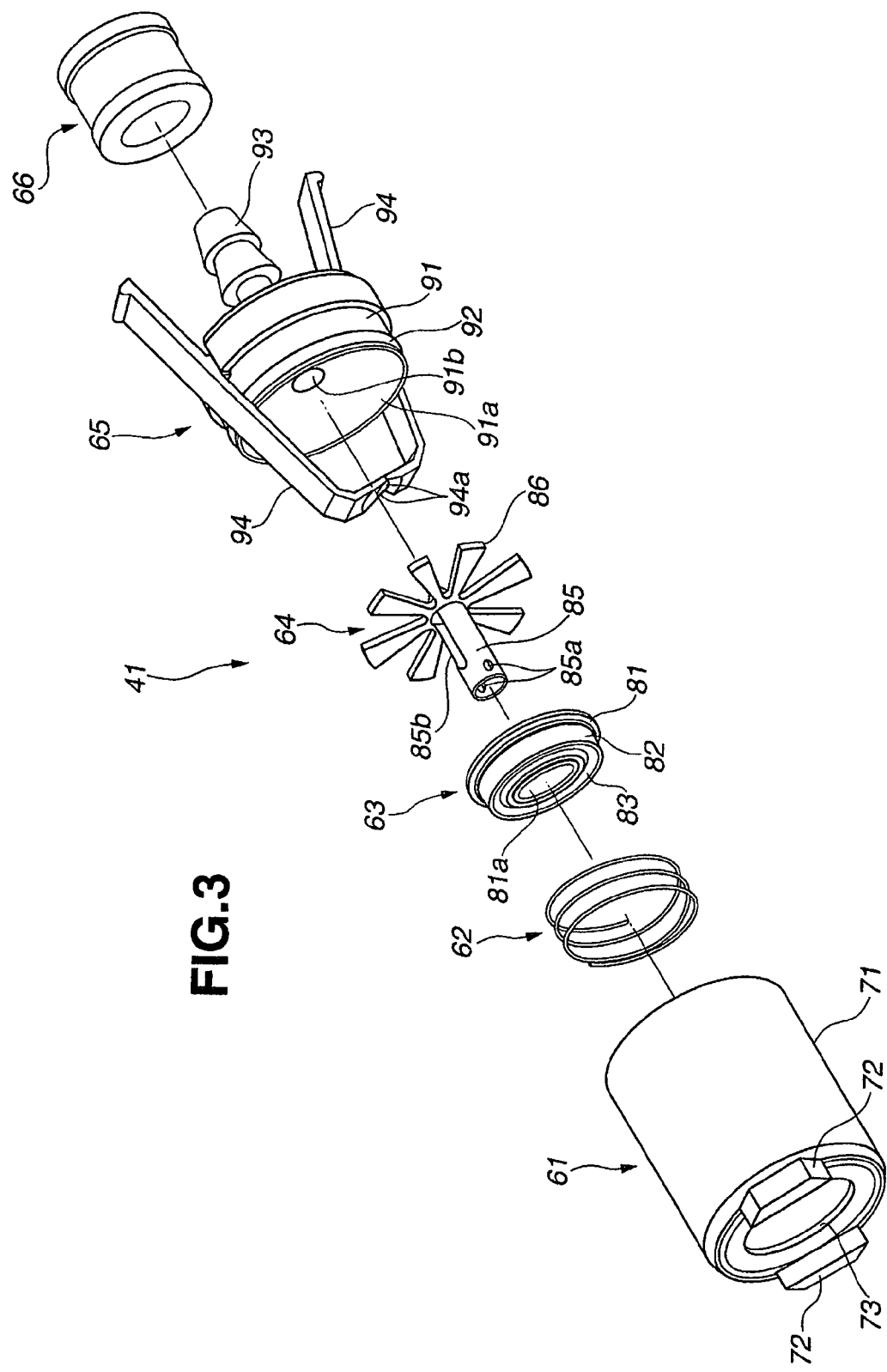
FIG. 3 is an exploded perspective view showing the endoscope side connector section of the washing tube according to the first embodiment.
Figure 4:
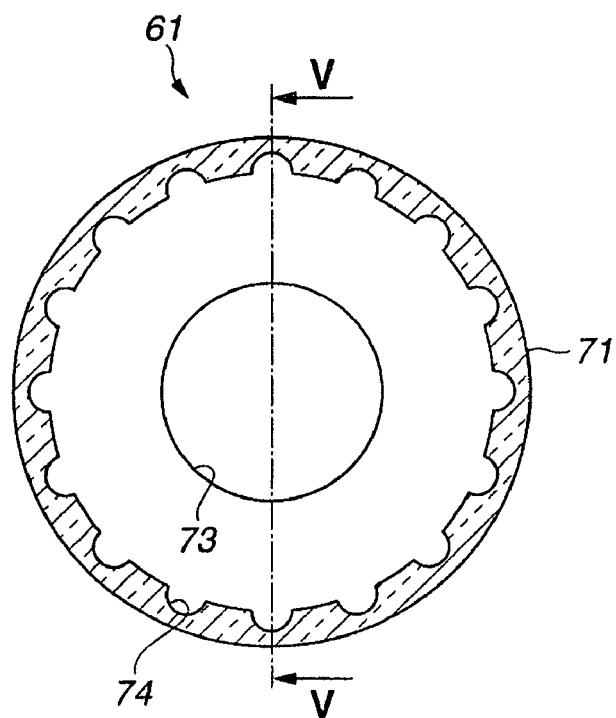
FIG. 4 is a cross-sectional view of the case body of the front case according to the first embodiment.
Figure 5:
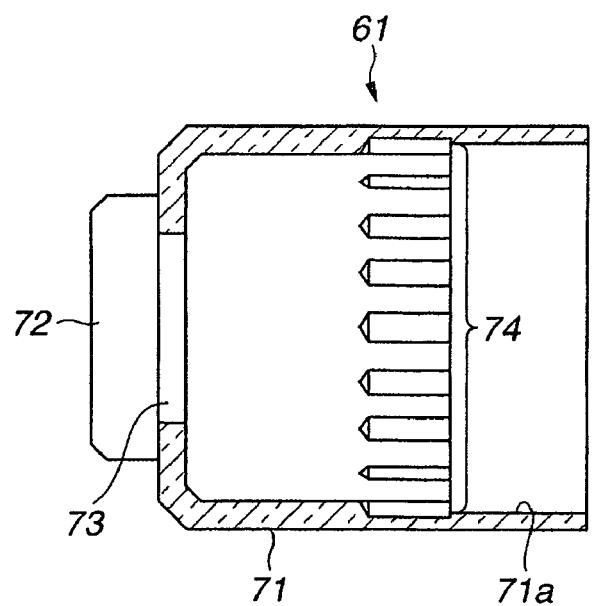
FIG. 5 is a cross-sectional view of the case body along line V-V of FIG. 4 according to the first embodiment.
Figure 6:
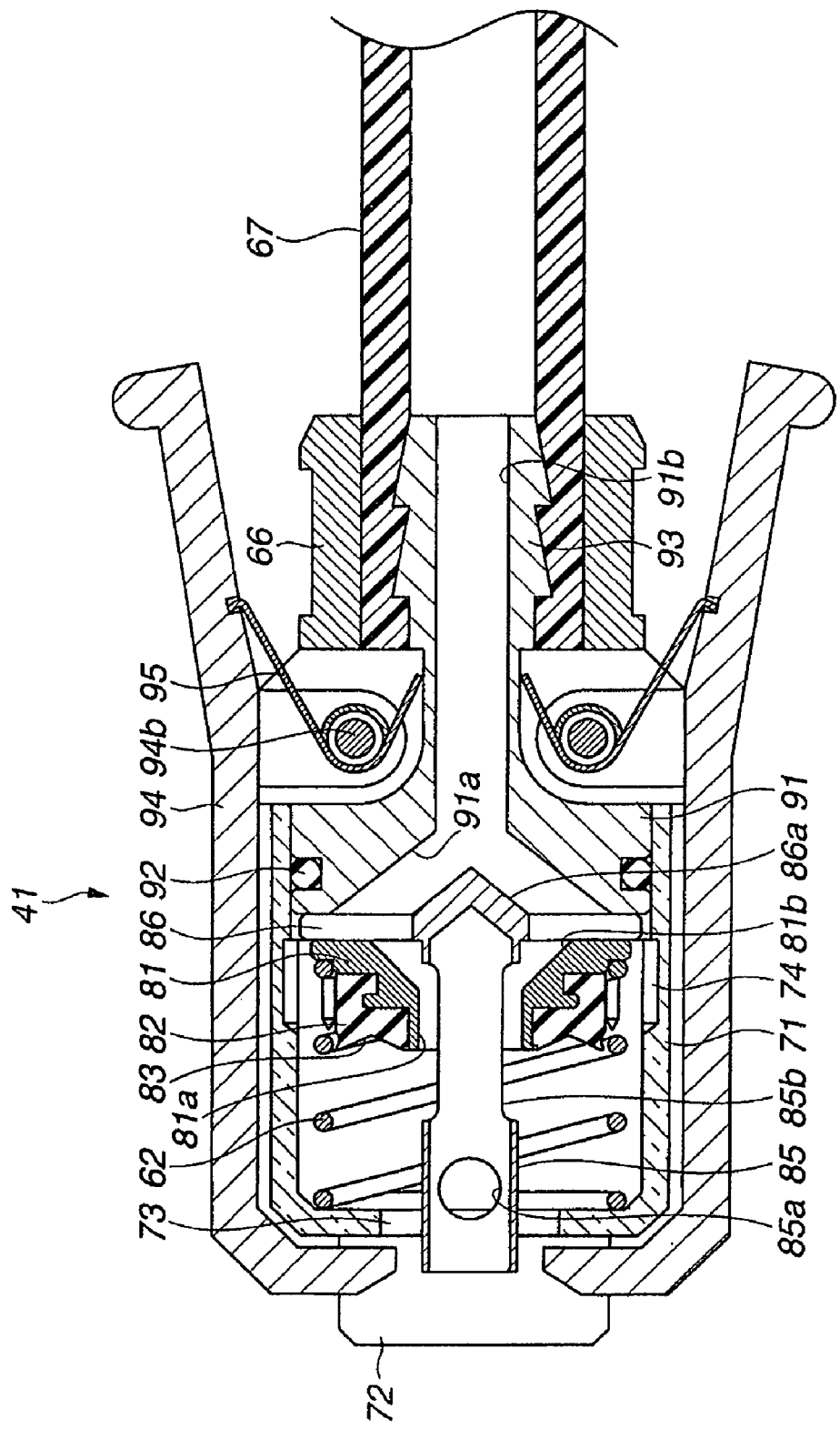
FIG. 6 is a cross-sectional view showing the endoscope side connector section of the washing tube according to the first embodiment.
Figure 7:
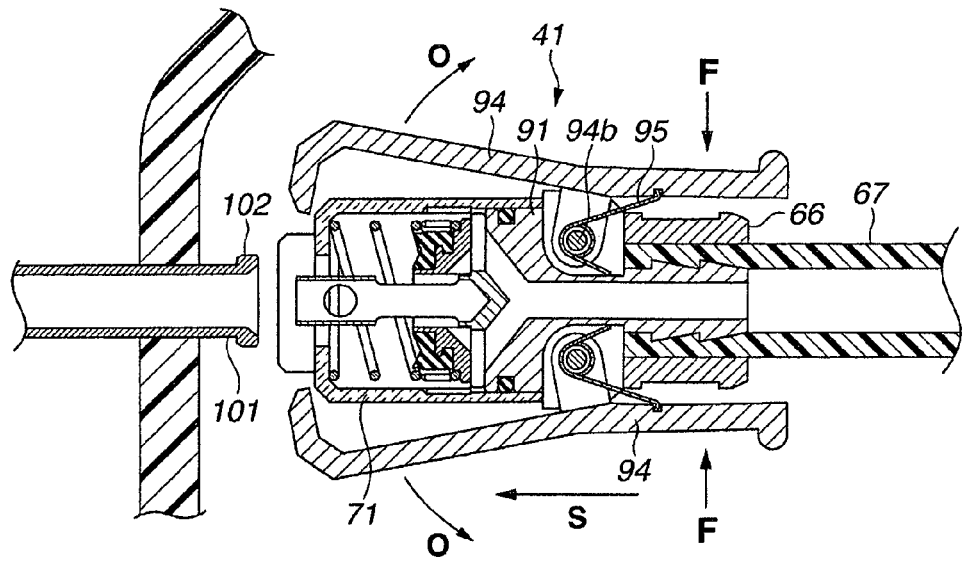
FIG. 7 is a cross-sectional view illustrating the operation of fitting the endoscope side connector section to the conduit base of the endoscope according to the first embodiment.
Figure 8:
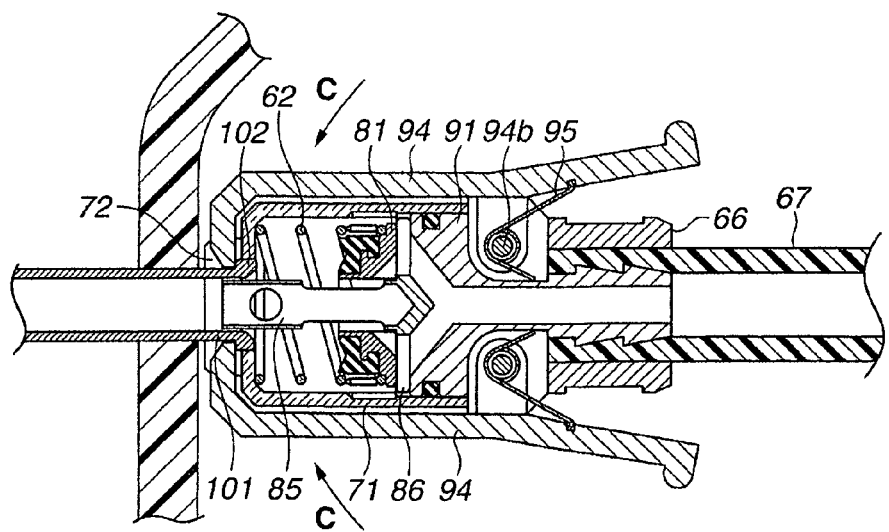
FIG. 8 is a cross-sectional view showing the endoscope side connector section fitted into the conduit base of the endoscope according to the first embodiment.
Figure 9:
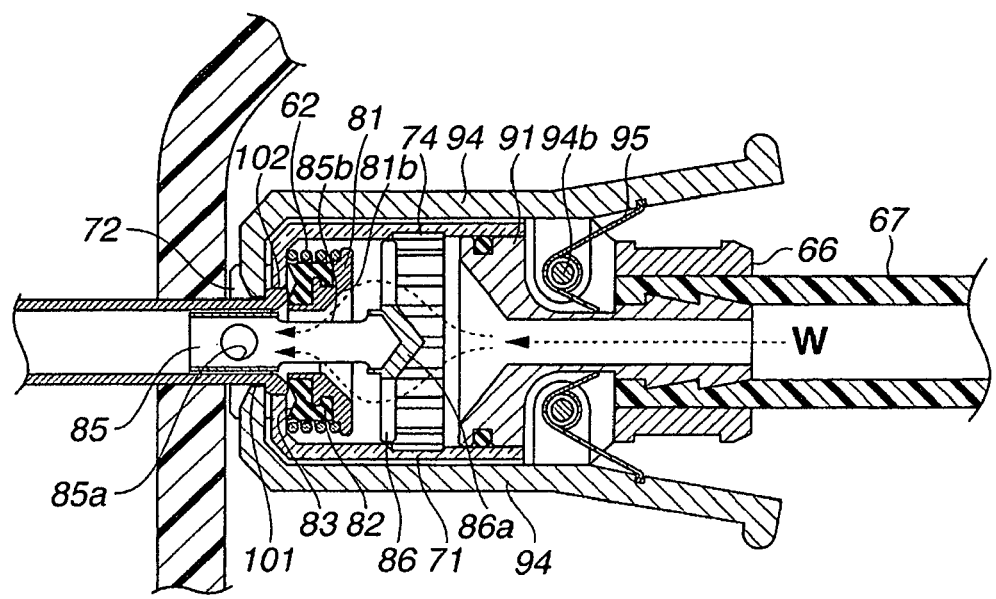
FIG. 9 is a cross-sectional view illustrating the operation of the endoscope side connector section during flow control according to the first embodiment.
Figure 10:
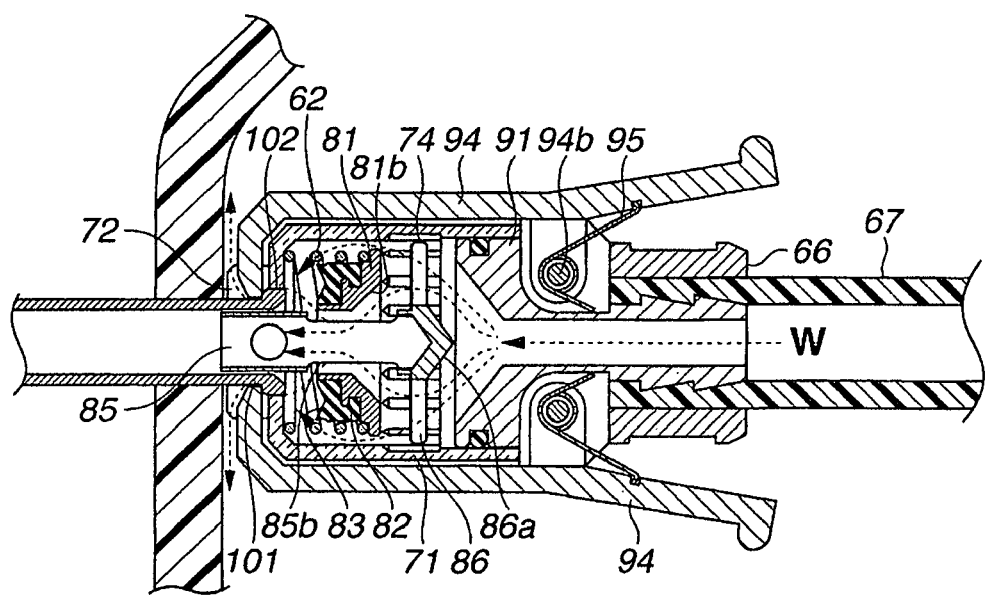
FIG. 10 is a cross-sectional view illustrating the operation of the endoscope side connector section according to the first embodiment when the outer surface of the conduit base is washed and disinfected.

FIG. 1 to FIG. 10 relate to the first embodiment of the present invention, FIG. 1 is a perspective view of an endoscope washing and disinfecting apparatus, FIG. 2 is a perspective view of the endoscope washing and disinfecting apparatus with the top cover in FIG. 1 left open so as to freely accommodate the endoscope in the washing and disinfecting tank, FIG. 3 is an exploded perspective view showing the endoscope side connector section of the washing tube, FIG. 4 is a cross-sectional view of the case body of the front case, FIG. 5 is a cross-sectional view of the case body along line V-V of FIG. 4, FIG. 6 is a cross-sectional view showing the endoscope side connector section of the washing tube, FIG. 7 is a cross-sectional view illustrating the operation of fitting the endoscope side connector section to the conduit base of the endoscope, FIG. 8 is a cross-sectional view showing the endoscope side connector section fitted into the conduit base of the endoscope, FIG. 9 is a cross-sectional view illustrating the operation of the endoscope side connector section during flow control and FIG. 10 is a cross-sectional view illustrating the operation of the endoscope side connector section when the outer surface of the conduit base is washed and disinfected.

As shown in FIG. 1 and FIG. 2, an endoscope washing and disinfecting apparatus 1 is an apparatus for washing and disinfecting a used endoscope 100 and the principal part thereof is constructed of an apparatus body 2 and a top cover 3, which is a cover disposed on and connected to the apparatus body 2 so as to be freely opened/closed via, for example, a hinge (not shown).

The endoscope washing and disinfecting apparatus 1 is configured in such a way that when the apparatus body 2 is covered with the top cover 3, the apparatus body 2 and the top cover 3 are fixed by, for example, a latch 8 disposed at positions of the apparatus body 2 and top cover 3 facing each other.

On the front side in the figure where the operator of the apparatus body 2 approaches (hereinafter referred to as "front side") and, for example, at the upper left half part, there is a detergent/alcohol tray 11 disposed in a manner freely drawable toward the front of the apparatus body 2.

The detergent/alcohol tray 11 accommodates a detergent tank 11a that stores a detergent which is a liquid used to wash an endoscope 100 and an alcohol tank 11b that stores alcohol which is a liquid used to dry the endoscope 100 after washing and disinfection and since the detergent/alcohol tray 11 is freely drawable, the respective tanks 11a and 11b can be refilled with liquids properly.

The detergent/alcohol tray 11 is provided with two windows 11m so that the operator can check the remaining quantity of detergent and alcohol put in the respective tanks 11a and 11b through the windows 11m. The detergent is a condensed detergent that can be diluted to a predetermined concentration with tap water subjected to sterilization processing by a feedwater filter. In the following explanations, the mixed liquid of the detergent and the tap water will be referred to as a "washing fluid" in the present embodiment.

Furthermore, on the front of the apparatus body 2 and, for example, at the upper right half part, there is a cassette tray 12 disposed in a manner freely drawable toward the front of the apparatus body 2. The cassette tray 12 accommodates a chemical solution bottle 12a filled with an undiluted solution of an antiseptic solution such as acetic peracid used to disinfect the endoscope 100 and since the cassette tray 12 is freely drawable, the cassette tray 12 allows the chemical solution bottle 12a to be set properly.

Furthermore, on the front of the apparatus body 2 and above the cassette tray 12 is disposed an operation sub-panel 13 on which buttons for displaying a washing and disinfecting time or indicating heating of the antiseptic solution or the like. Furthermore, at the front bottom of the apparatus body 2 in the figure is disposed a pedal switch 14 to cause the top cover 3 disposed at the top of the apparatus body 2 in a closed position to open upward when the operator steps on the pedal switch 14 as shown in FIG. 2.

Furthermore, as shown in FIG. 2, at the top surface of the apparatus body 2, for example, close to both ends of the front side that the operator approaches is provided a main operation panel 25 where setting switches such as a washing and disinfection operation start switch and a washing and disinfection mode selection switch of the apparatus body 2 are arranged.

Furthermore, on the top surface of the apparatus body 2 and on one side facing the front that the operator approaches disposed a feedwater hose connection section 31 to which a hose connected to a water tap is connected in order to feed tap water to the apparatus body 2. The feedwater hose connection section 31 may also be disposed with a filter for filtering tap water.

Furthermore, at substantially the center of the top surface of the apparatus body 2 is provided a washing and disinfecting tank 4 in which the endoscope 100 is accommodated, where the opening for accommodating the endoscope is closed/opened by the top cover 3. The washing and disinfecting tank 4 is made up of a tank body 50 and a terrace section 51 provided continuously around the perimeter of the opening for accommodating the endoscope of the tank body 50.

The tank body 50 can accommodate the endoscope 100 when the used endoscope 100 is washed and disinfected and a bottom face 50t which is the surface inside the tank body 50 is provided with a drain outlet 55 to drain a washing fluid, water, alcohol, antiseptic solution or the like supplied to the tank body 50 from the tank body 50.

Furthermore, at any given position of peripheral side 50s, which is the surface inside the tank of the tank body 50, is provided a circulation port 56 for supplying the washing fluid, water, alcohol, antiseptic solution or the like having been supplied to the tank body 50 from the tank body 50 to various conduits disposed inside the endoscope 100 through a washing tube 40 which will be described later or for supplying the above described liquid from a feedwater circulation nozzle 24 which will be described later to the tank body 50 again through a filter or the like. The circulation port may also be provided with a filter for filtering washing fluid, water, alcohol, antiseptic solution or the like.

The above described circulation port 56 may also be provided in the bottom face 50*t* of the tank body 50. The circulation port 56 provided in the bottom face 50*t* of the tank body 50 will allow the washing fluid, water, alcohol, antiseptic solution or the like having been supplied to the tank body 50 to be drained from the tank body 50 more quickly than the circulation port 56 provided in the side 50*s*.

This will further speed up the supply of the washing fluid, water, alcohol, antiseptic solution or the like to each conduit of the endoscope 100 or the tank body 50 again. The circulation port 56 provided in the bottom face also has an advantage of allowing the operator to easily approach the filter or the like provided for the circulation port 56 when the user replaces the filter or the like.

The washing and disinfecting tank 4 is provided with an ultrasound transducer (not shown in FIG. 2) and a heater (not shown) on the back side of the tank body 50, and a washing case 6 at a conduit disinfection port 7 disposed at substantially the center of the bottom face 50*t* of the tank body 50. The ultrasound transducer is intended to give vibration to washing water or tap water stored in the washing and disinfecting tank 4 to wash or rinse the outer surface of the endoscope 100 with ultrasound. On the other hand, the heater is intended to heat the washing fluid, tap water or the like stored in the washing and disinfecting tank 4 to a predetermined temperature.

A washing case 6 is intended to accommodate buttons such as various scope switches of the endoscope 100 and removable parts provided for the endoscope 100 so as to be washed and disinfected together with the endoscope 100. A conduit disinfection port 7 is intended to supply an antiseptic solution to the conduit inside the apparatus through a washing and disinfection hose (not shown) to disinfect the feedwater tube.

At any given position of the side 50*s* of the tank body 50 is provided a water level sensor 32 with a cover to detect the water level of the washing fluid, water, alcohol, antiseptic solution or the like supplied to the tank body 50.

On the surface of the terrace section 51 other than a terrace surface 51*t*, that is, surface parallel to the bottom face 50*t* of the tank body 50 are provided a detergent nozzle 22 to supply a detergent to be diluted to a predetermined concentration with tap water to the tank body 50 from the detergent tank 11*a* through a pump (not shown) and an antiseptic solution nozzle 23 to supply an antiseptic solution from the chemical solution bottle 12*a* from an antiseptic solution tank (not shown) for diluting and mixing an undiluted solution of the injected antiseptic solution through a pump (not shown).

Furthermore, on a surface of the terrace section 51 parallel to the bottom face 50*t* of the tank body 50 is provided a feedwater circulation nozzle 24 for supplying alcohol to the tank body 50 from the alcohol tank 11*b* through a pump (not shown in FIG. 2) or supplying washing fluid, water, alcohol, antiseptic solution or the like drained from the circulation port 56 of the tank body 50 to the tank body 50 again. The detergent nozzle 22, the antiseptic solution nozzle 23 and the feedwater circulation nozzle 24 may also be provided on the terrace surface 51*t*.

Furthermore, on a surface 51*f* on the side of the terrace surface 51*t* of the terrace section 51 opposed to an operator approaching position 4*k* are provided a plurality of, here two, air/water supply/forceps ports 33 which are fluid supply sections for supplying washing fluid, water, alcohol, antiseptic solution, air or the like to the channel which is the endoscope conduit provided inside the endoscope 100, a forceps raising port 34, and a water leakage detection port 35.

Apparatus side connectors disposed at one end of the washing tubes 40 are fitted to the two air/water supply/forceps ports 33 and forceps raising port 34 respectively and endoscope side connectors 41 (see FIG. 3) which are the connector sections of the present embodiment disposed at the other end of the washing tubes 40 are fitted to the conduit bases which become the channel connector sections of the endoscope 100.

Furthermore, the endoscope washing and disinfecting apparatus 1 of the present embodiment is provided with a flow control function that detects conduit clogging inside the channel of the endoscope 100 during washing and disinfection. Since the specific configuration and operation of the flow control function are arts conventionally used, detailed explanations thereof will be omitted.

Next, the endoscope side connector 41 of the washing tube 40 will be explained in detail below based on FIG. 3 to FIG. 6. In the following explanations, the direction in which the endoscope side connector 41 is connected to the conduit base which becomes the channel connector section of the endoscope 100 is assumed to be the front side.

The endoscope side connector 41 is constructed of a quasi-cylindrical front case 61, a spring 62, an annular valve body 63, a bladed tubular body 64, a sealing tubular body 65, and a clamping tube 66.

The front case 61 is provided with two projections 72 protruding on the front of a case body 71 and the projections 72 are disposed so as to face each other across a front opening 73. Furthermore, a plurality of recessed parts 74 are formed back to back in the circumferential direction of the inner surface of the case body 71 and a step 71*a* is formed so that the hole diameter of the inner surface on the back side of the recessed parts 74 is greater in the circumferential direction (see FIG. 4 and FIG. 5).

The spring 62 is an elastic member (biasing member) to bias the valve body 63 backward inside the case body 71.

The valve body 63 is configured by including an annular section 81 which is a hard annular member with an outward flange formed at the back and a sealing body 82 which is a sealing member made of an elastic member such as annular rubber extrapolated around the annular section 81. Furthermore, a recessed part 83 which is dented backward in the circumferential direction is formed on the front of the sealing body 82. The valve body 63 is accommodated into the case body 71 of the front case 61 in a manner freely movable back and forth with a backward biasing force always given by the spring 62 contacting the outward flange (see FIG. 6). Furthermore, a hole 81*a* is formed in the center of the annular section 81 of the valve body 63. Furthermore, a conic surface 81*b* tapered toward the front is formed in the center of the back end face of the annular section 81 so as to communicate with the hole 81*a*. That is, the valve body 63 moves forward against the biasing force of the spring 62 when the tapered surface 81*b* and the surface parallel to a water flow around the tapered surface 81*b* become resisting surfaces, a passing fluid hits the surfaces and flows into the hole 81*a*. FIG. 7 illustrates a shape including the tapered surface as an example of the resisting surface, but the present suggestion is not limited to this and the resisting surface may have a shape not including any tapered surface, that is, a shape made up of only a surface perpendicular to the water flow. Furthermore, the resisting surface may also have a shape made up of only a tapered surface.

The bladed tubular body 64 is configured by including a quasi-cylindrical cylindrical section 85 on the front side and a plurality of blades 86 uniformly and radially arranged behind the cylindrical section 85. On the perimeter of the cylindrical section 85 are disposed two circular holes 85*a* formed at the front and two long holes 85b formed backward up to the blades 86 at positions shifted by 90° from the two holes 85a. Furthermore, when accommodated into the case body 71 of the front case 61, the cylindrical section 85 of the bladed tubular body 64 is loosely fitted into the hole 81a of the annular section 81 of the valve body 63 and inserted in a manner freely movable back and forth so as to protrude from the opening 73 of the case body 71 (see FIG. 6). Furthermore, a conic tapered section 86a is formed in the bladed tubular body 64 at the central rear end which forms the root of the plurality of blades 86.

The sealing tubular body 65 is configured by including a quasi-annular sealing body 91, an O-ring 92 which is a sealing member fitted around the perimeter of the sealing body 91, a tube connector section 93 extending from the center of the back end face of the sealing body 91 and two clip bodies 94 disposed so as to face each other at point-symmetric positions on the perimeter with respect to the center of the sealing body 91.

A conic tapered surface 91a is formed backward at the front of the sealing body 91 and a hole 91b is formed in the back end face of the tube connector section 93. The sealing body 91 is fitted so that an O-ring 92 comes into close contact with the above described step 71a from the rear opening of the case body 71 of the front case 61 and fixed to the case body 71 by a screw (not shown) with the joint surface kept watertight (see FIG. 6).

The two clip bodies 94 are formed so that the respective front sides extend in directions along the central axis of the sealing body 91 and arc-shaped notches 94a are formed at their extending ends. Furthermore, the two clip bodies 94 are disposed in a manner pivotable around a rotation axis 94b of the sealing body 91 respectively and are biased in a direction along the central axis of the sealing body 91 by torsion springs 95 (see FIG. 6). That is, the two clip bodies 94 are biased by the torsion springs 95 in a closed state in a direction in which the front extending parts approach and come into contact with each other around the rotation axis 94b.

Furthermore, one end of a tube body 67 is connected to the tube connector section 93 of the sealing body 91 and the clamping tube 66 is fitted around the perimeter of one end of the tube body 67. In this way, in the washing tube 40, the endoscope side connector 41 configured as shown above is disposed at one end of the tube body 67.

The apparatus side connectors disposed at the other end of the washing tube 40 detachably connected to the air/water supply/forceps ports 33 and forceps raising port 34 are the same as the conventional ones, and therefore detailed explanations of configurations thereof will be omitted.

Next, the operation of the endoscope side connector 41 of the washing tube 40 will be explained in detail below based on FIG. 7 to FIG. 10.

First, as shown in FIG. 7, when the endoscope side connector 41 of the washing tube 40 is connected to a conduit base 101 of the endoscope 100, the back end portions of the clip bodies 94 are pressed down by fingers. In this case, the respective clip bodies 94 receive forces in the opposed directions indicated by an arrow F and thereby rotate in a direction indicated by an arrow O around the rotation axis 94b against the biasing force of the torsion springs 95 and the front parts open so as to move apart from each other.

In this condition, the endoscope side connector 41 is moved in a direction indicated by an arrow S toward the conduit base 101 of the endoscope 100, the conduit base 101 is loosely fitted into the opening 73 of the case body 71 of the front case 61 and the respective clip bodies 94 are released from the gripped state. Each clip body 94 is then rotated around the rotation axis 94b in a direction indicated by an arrow C shown in FIG. 8 by the biasing force of the torsion spring 95 so that the front end parts come closer to each other and catch the conduit base 101.

In this case, the arc-shaped notch 94a of each clip body 94 (see FIG. 3) comes into contact with the perimeter of the conduit base 101 and engages with an outward flange 102 formed at the end face perimeter of the conduit base 101. In this way, the endoscope side connector 41 of the washing tube 40 is fitted to the conduit base 101 of the endoscope 100.

The two projections 72 disposed on the front of the case body 71 of the front case 61 are intended to come into contact with the wall of the endoscope 100 to thereby prevent the conduit base 101 from excessively going into the front case 61 and define the position at which each clip body 94 catches the conduit base 101. Furthermore, when the endoscope side connector 41 is fitted to the conduit base 101, the front end of the cylindrical section 85 of the bladed tubular body 64 is inserted into the conduit base 101.

As described above, the endoscope side connector 41 of the washing tube 40 is fitted to the conduit base 101 of the endoscope 100 and the endoscope 100 is mounted properly in the washing and disinfecting tank 4. In this way, the endoscope washing and disinfecting apparatus 1 of the present embodiment washes and disinfects the used endoscope 100 according to a predetermined programming. Since various steps of washing and disinfection of the endoscope 100 by the endoscope washing and disinfecting apparatus 1 are conducted in steps similar to conventional ones, detailed explanations thereof will be omitted.

Furthermore, as described above, the endoscope washing and disinfecting apparatus 1 performs flow control to detect conduit clogging inside the channel of the endoscope 100. During the flow control, as shown in FIG. 9, in the endoscope side connector 41 of the washing tube 40, a predetermined pressure corresponding to the flow rate of a liquid W such as a washing fluid sent from the tube body 67 causes the annular section 81 of the valve body 63 to move forward against the biasing force of the spring 62 and the sealing body 82 comes into close contact with the surface of the conduit base 101 and the perimeter of the opening of the case body 71 of the front case 61 and thereby prevents leakage of the liquid W.

More specifically, in the valve body 63, the tapered surface 81b formed on the back surface of the annular section 81 is given a predetermined pressure corresponding to the flow rate of the liquid W. The annular section 81 then moves forward together with the sealing body 82. The endoscope washing and disinfecting apparatus 1 of the present embodiment sets a flow rate at which the liquid W by a liquid sending pump (not shown) is sent so that the predetermined pressure which the valve body 63 receives from the liquid W is greater than the biasing force of the spring 62.

The sealing body 82 of the valve body 63 which has moved forward comes into contact with the surface of the conduit base 101 of the endoscope 100 and also comes into contact with the perimeter inner surface of the opening 73 of the case body 71 of the front case 61. Even when there is a difference in level between the surface of the conduit base 101 and the perimeter inner surface of the opening 73 of the case body 71, elastic deformation of the recessed parts 83 formed in the front of the sealing body 82 causes the sealing body 82 to come into close contact with the surface of the conduit base 101 and the perimeter inner surface of the opening 73 of the case body 71 to keep watertightness so as to prevent the liquid W from leaking into the gap between the conduit base 101 and the opening 73 of the case body 71.

Furthermore, the bladed tubular body 64 also moves forward under the pressure of the liquid W. In this case, the liquid W passes between the plurality of blades 86 of the bladed tubular body 64, flows into the two long holes 85b formed in the cylindrical section 85 and is all sent from the front opening of the cylindrical section 85, two holes 85a, and the perimeter of the cylindrical section 85 into the conduit base 101. The plurality of recessed parts 74 formed in the inner surface of the case body 71 of the front case 61 are intended to facilitate the smooth flow of the passing liquid W.

As described above, during flow control by the endoscope washing and disinfecting apparatus 1, since the liquid W sent such as washing fluid is all supplied into the channel of the endoscope 100 through the washing tube 40 and conduit base 101 without leaking from the endoscope side connector 41, it is possible to normally detect conduit clogging inside the channel.

On the other hand, when flow control is not performed, the endoscope side connector 41 of the washing tube 40 is designed as shown in FIG. 10 so that the liquid W such as washing fluid leaks through the opening of the case body 71 of the front case 61 to wash and disinfect the surface of the conduit base 101.

More specifically, for the endoscope washing and disinfecting apparatus 1 of the present embodiment, a flow rate for sending the liquid W by the liquid sending pump (not shown) is set in such a way that the pressure which the valve body 63 receives from the liquid W becomes smaller than the biasing force of the spring 62. That is, even if the tapered surface 81b formed on the back surface of the annular section 81 is given a pressure from the liquid W, the valve body 63 still moves slightly forward while receiving the biasing force of the spring 62, yet stops at a position where the valve body 63 does not come into contact with the surface of the conduit base 101 of the endoscope 100 and the perimeter inner surface of the opening 73 of the case body 71 of the front case 61. At this moment, the liquid W flows and leaks through the gap between the conduit base 101 and the opening 73 of the case body 71.

As described above, while flow control is not being conducted, it is possible to wash and disinfect the outer surface of the conduit base 101 and the root of the conduit base 101 protruding from the wall of the endoscope 100.

As described above, the endoscope washing and disinfecting apparatus 1 of the present embodiment is configured to be able to wash and disinfect also the outer surface of the conduit base 101 which is the channel opening of the used endoscope 100, improve the accuracy of flow control to detect conduit clogging inside the channel and perform normal detection.

Furthermore, using the washing tube 40 of the present embodiment, the endoscope washing and disinfecting apparatus 1 needs only to distinguish between flow control and other modes and control the flow rate of the liquid sending pump for sending a washing fluid or the like, and can thereby simplify the configuration compared with the technique of an attaching/detaching mechanism or the like of the conventional washing fluid supply nozzle in particular and obtain the above described effects.

Second Embodiment

Figure 11:
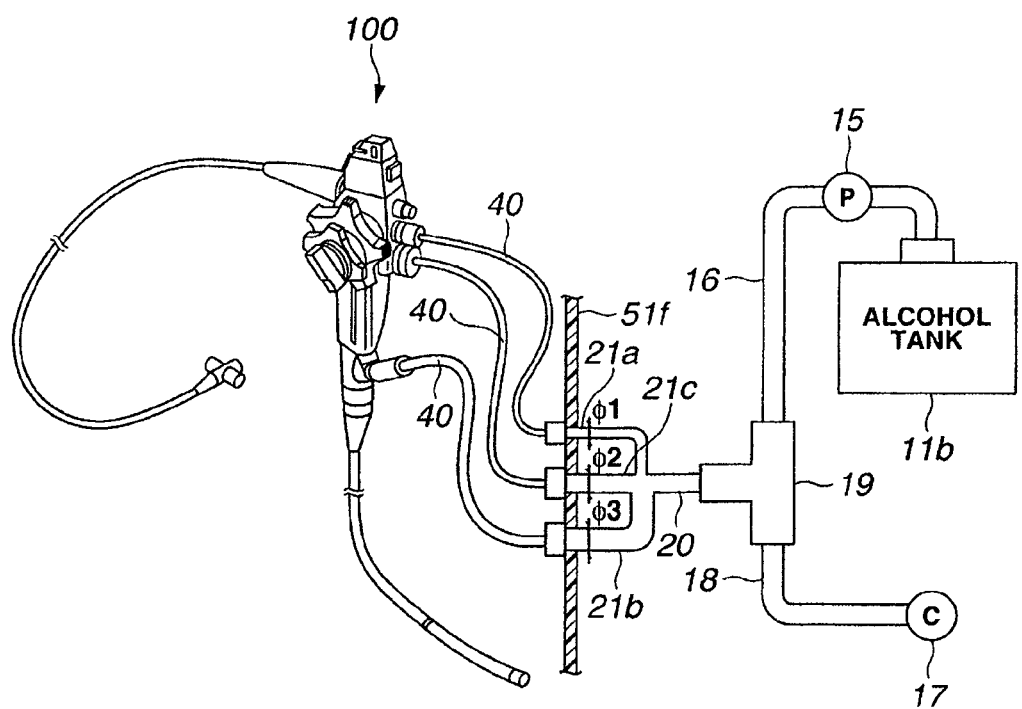
FIG. 11 is a schematic diagram showing a conduit configuration for supplying alcohol from an alcohol tank to a channel of an endoscope according to a second embodiment.

Next, based on FIG. 11, a second embodiment of the present invention will be explained. FIG. 11 is a schematic diagram showing the conduit configuration for supplying alcohol from the alcohol tank to the channel of the endoscope according to the second embodiment of the present invention.

In the following explanations, the same components as those of the endoscope washing and disinfecting apparatus 1 of the above described first embodiment will be assigned the same reference numerals and detailed explanations thereof will be omitted.

Here, conventional endoscope washing and disinfecting apparatuses are known to perform an alcohol flushing step to prompt drying inside the channel of the endoscope. In the alcohol flushing step, the conventional endoscope washing and disinfecting apparatus is configured to send alcohol stored in an alcohol tank into an MIX block in the apparatus through an alcohol pump and send alcohol into each channel of the endoscope using a compressor. In this case, since the channel diameter of the channel of the endoscope varies depending on the use, the amount of alcohol to be sent into each channel may vary, which results in a problem that a large quantity of alcohol needs to be sent.

Therefore, an example of the endoscope washing and disinfecting apparatus 1 of the present embodiment will be shown below, which is capable of efficiently and stably supplying even a small quantity of alcohol used in an alcohol flushing step to various channels of the endoscope of different diameters and prompting drying inside the channels.

As shown in FIG. 11, as for the endoscope washing and disinfecting apparatus 1 according to the present embodiment, one end of an alcohol conduit 16 is connected to an alcohol tank 11b. An alcohol pump 15 is interposed between the alcohol tank 11b and the other end of the alcohol conduit 16, which is connected to an air-liquid mixing nozzle 19.

One end of an air-supply conduit 18 is also connected to the air-liquid mixing nozzle 19 and a compressor is connected to the other end of the air-supply conduit 18. Furthermore, an aggregate end of a trifurcated channel conduit 20 is also connected to the air-liquid mixing nozzle 19 here.

The channel conduit 20 is connected to the two air/water supply/forceps ports 33 and forceps raising port 34 provided on the surface 51f of the terrace surface 51t of the terrace section 51 shown in FIG. 2, to which three branch conduits 21a to 21c correspond.

Furthermore, here, the conduit diameter $\Phi 1$ of the first branch conduit 21a communicating with one of the air/water supply/forceps ports 33 is the smallest, the conduit diameter $\Phi 2$ of the second branch conduit 21b communicating with the other air/water supply/forceps port 33 is the next smallest and the conduit diameter $\Phi 3$ of the third branch conduit 21c communicating with the forceps raising port 34 is the largest ($\Phi 1 < \Phi 2 < \Phi 3$).

In the endoscope washing and disinfecting apparatus 1 of the present embodiment configured as described above, alcohol is suctioned by the alcohol pump 15 from the alcohol tank 11b in the alcohol flushing step and supplied to the air-liquid mixing nozzle 19 via the alcohol conduit 16. At the same time, air from the compressor 17 is supplied to the air-liquid mixing nozzle 19 via the air-supply conduit 18.

The air-liquid mixing nozzle 19 mixes the supplied alcohol and air, atomizes alcohol and sprays alcohol into the channel conduit 20. The atomized alcohol is sent to the respective branch conduits 21a to 21c so as to spread into every corner of the channel conduit 20 and supplied into the respective channels of the endoscope 100 via the washing tubes 40.

Thus, the alcohol sprayed by the air-liquid mixing nozzle 19 is similar to gas, can thereby be uniformly supplied to the respective branch conduits 21a to 21c of different conduit diameters $\Phi$ and uniformly supplied to the respective washing tubes 40 of different tube diameters and the respective channels of different channel diameters of the endoscope 100. Furthermore, even if the channel conduit 20 has a complicated configuration or sends a liquid vertically upward, it is possible to supply atomized alcohol stably and uniformly.

As described above, the endoscope washing and disinfecting apparatus 1 of the present embodiment atomizes alcohol and efficiently sprays alcohol into the respective conduits, and is therefore configured to be able to execute an alcohol flushing step to prompt drying with a small quantity of alcohol.

Third Embodiment

Figure 12:
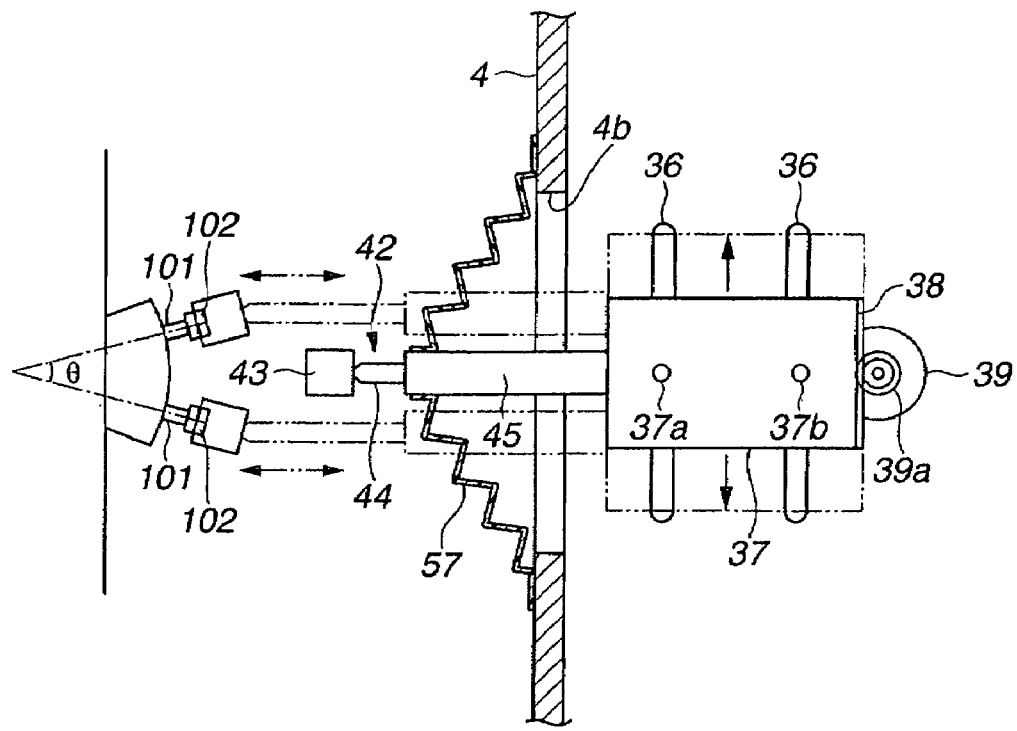
FIG. 12 is a partial cross-sectional view showing a configuration of an endoscope conduit automatic attaching/detaching mechanism according to a third embodiment that moves in two directions, upward and downward, by a motor and moves forward/backward toward/from the conduit base of the endoscope.
Figure 13:
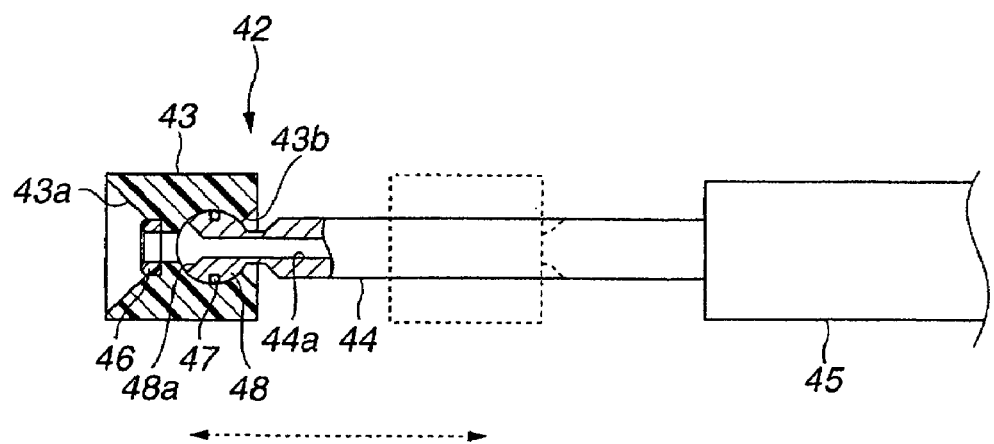
FIG. 13 is a partial cross-sectional view showing a configuration of a nozzle unit according to the third embodiment.
Figure 14:
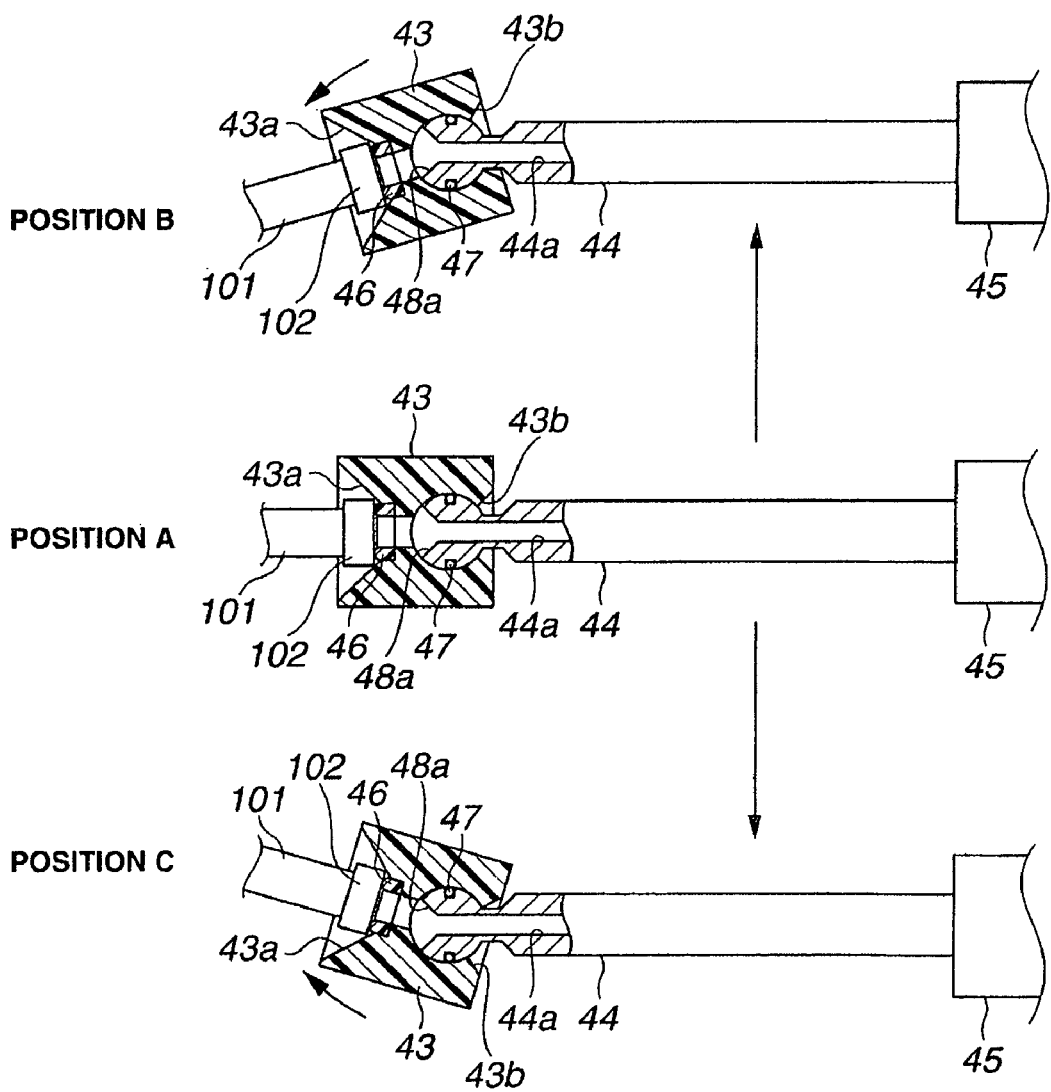
FIG. 14 is a partial cross-sectional view illustrating the operation of the nozzle unit according to the third embodiment.
Figure 15:
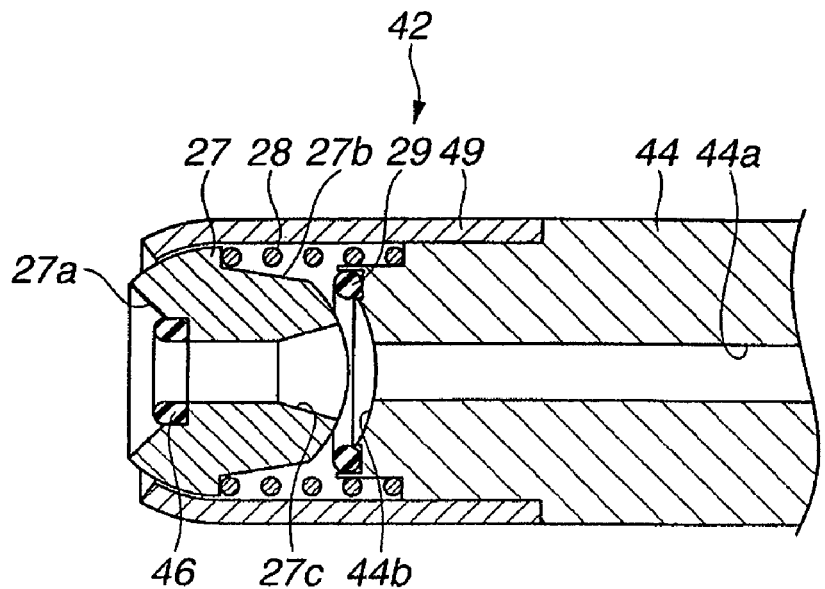
FIG. 15 is a partial cross-sectional view showing a configuration of a nozzle unit of a modification example according to the third embodiment.
Figure 16:
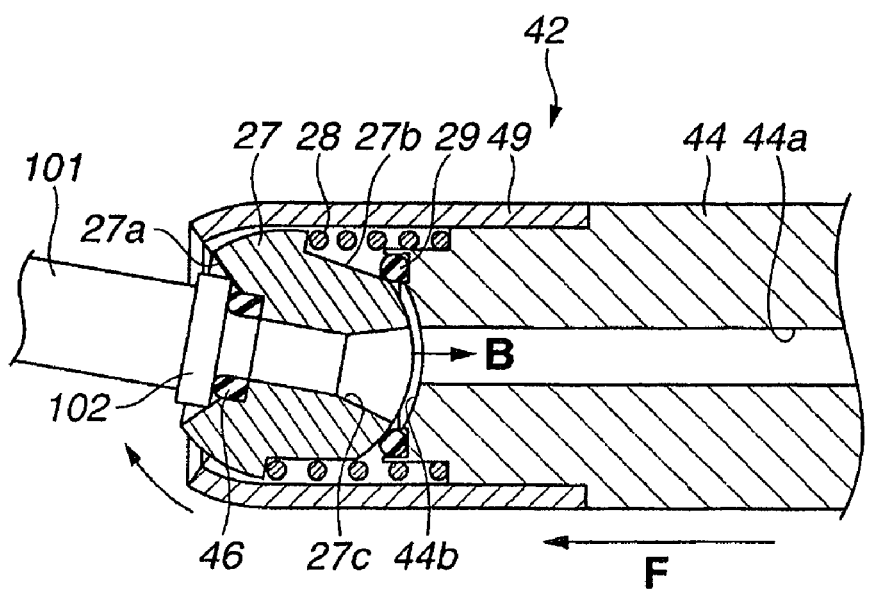
FIG. 16 is a partial cross-sectional view illustrating the operation of the nozzle unit in FIG. 15 according to the third embodiment.

Next, a third embodiment of the present invention will be explained based on FIG. 12 to FIG. 16. FIG. 12 to FIG. 16 relate to the third embodiment of the present invention, FIG. 12 is a partial cross-sectional view showing a configuration of an endoscope conduit automatic attaching/detaching mechanism that moves in two directions; upward and downward, by a motor and moves forward/backward toward/from the conduit base of the endoscope, FIG. 13 is a partial cross-sectional view showing a configuration of a nozzle unit, FIG. 14 is partial cross-sectional view illustrating the operation of the nozzle unit, FIG. 15 is a partial cross-sectional view showing a configuration of a nozzle unit of a modification example, and FIG. 16 is a partial cross-sectional view illustrating the operation of the nozzle unit in FIG. 15.

In the following explanations, the same components as those of the endoscope washing and disinfecting apparatus 1 of the above described first embodiment will be assigned the same reference numerals and detailed explanations thereof will be omitted.

Incidentally, there are conventional endoscope washing and disinfecting apparatuses known to move a washing nozzle forward/backward to/from a conduit base which corresponds to the opening of the channel of the endoscope so as to automatically attach/detach the washing nozzle. Depending on the type, however, not only endoscopes have a different number of channels and different locations of the conduit bases, but also when there are a plurality of conduit bases, the respective conduit bases have predetermined angles and are tilted in different directions. When a treatment instrument or the like is inserted into the channel via the conduit base, this is a configuration that takes account of ease of insertion of the treatment instrument.

However, the conventional endoscope washing and disinfecting apparatus needs to be provided with washing nozzles corresponding to an attachment/detachment position of a conduit base of an endoscope having one channel and attachment/detachment positions of conduit bases of an endoscope having a plurality of channels, which results in a problem with increases in cost and size of the apparatus. Moreover, when a plurality of conduit bases are provided, the respective conduit bases have predetermined angles and are tilted in different directions, which results in a problem that the mechanism of automatic attachment/detachment to/from the conduit bases becomes complicated.

Therefore, an example of the endoscope washing and disinfecting apparatus 1 according to the present embodiment will be shown below, which can be automatically attached/detached to/from conduit bases corresponding in number to channels of an endoscope to be washed and attached/detached to/from a plurality of (two in the following explanations) conduit bases, each having a predetermined angle and being tilted in a direction different from each other. In this way, the endoscope washing and disinfecting apparatus of the present embodiment has an advantage of having a simple configuration, being able to be manufactured at low cost and preventing the size of the apparatus from increasing.

The endoscope washing and disinfecting apparatus 1 of the present embodiment adopts a configuration in which a nozzle unit 42 is moved forward/backward to/from each conduit base 101 of a plurality of channels provided for the endoscope 100 by a pressure of a fluid such as washing fluid so as to be attached/detached.

More specifically, as shown in FIG. 12, the endoscope washing and disinfecting apparatus 1 is provided with the nozzle unit 42 loosely fitted into a hole 4b provided in the wall of the washing and disinfecting tank 4 so as to be able to move in two directions (vertical direction in FIG. 12) within a range of the hole 4b. Furthermore, the nozzle unit 42 is accommodated in a nozzle housing tube 45 and the nozzle housing tube 45 is connected to a box body 37 in an airtight manner. A tube conduit (not shown) for supplying a fluid such as washing fluid is connected to the box body 37.

The distal end portion of the nozzle housing tube 45 is disposed so as to penetrate a bellows-like watertight sealing member 57 in a watertight manner. Furthermore, the watertight sealing member 57 is fixed so as to keep the hole 4b of the washing and disinfecting tank 4 watertight.

The box body 37 is provided with a gear groove 38 which serves as a rack on a back end face and the gear groove 38 engages with a motor gear 39a of a motor 39 serving as a pinion. Furthermore, the box body 37 is provided with two pin members 37a which are engaged with two rails 36 provided inside the apparatus body 2 and guided so as to move straight. That is, the box body 37 is driven by the motor 39 so as to move along the two rails 36 in two directions, upward and downward in FIG. 12.

In conjunction with this, the nozzle housing tube 45 connected to the box body 37 also moves in two directions, upward and downward in FIG. 12. The driving of the box body 37 by the motor 39 is controlled by a control section inside the apparatus body 2 and the nozzle unit 42 fitted to the nozzle housing tube 45 is set so as to move to two respective positions of the two conduit bases 101 of the endoscope 100. Furthermore, the present embodiment sets the amount of movement of the box body 37 in two directions corresponding to the movement of the nozzle unit 42 to the positions of the two conduit bases 101 by setting the number of revolutions of the motor gear 39a of the motor 39.

That is, when the nozzle unit 42 moves to and stops at a position corresponding to one conduit base 101, a conduit connector 43 shown in FIG. 13 moves forward, when a fluid is supplied to the nozzle housing tube 45 via the box body 37, together with the nozzle conduit 44 which receives the pressure of the fluid and is connected to the one conduit base 101. Likewise, when the nozzle unit 42 moves to and stops at a position corresponding to the other conduit base 101, the conduit connector 43 moves forward, when a fluid is supplied to the nozzle housing tube 45 via the box body 37, together with the nozzle conduit 44 which receives the pressure of the fluid and is connected to the other conduit base 101. When the endoscope 100 has, for example, two conduit bases 101 as shown in FIG. 12, the conduit bases 101 are disposed so as to form an angle θ with each other and spread in the direction of the opening.

Furthermore, the conduit connector 43 is pivotably disposed at an end of the nozzle conduit 44 as shown in FIG. 13.

More specifically, a spherical coupling section 48 is provided at the end of the nozzle conduit 44. A conical surface 48a tapered backward is formed in the coupling section 48 around the perimeter of the opening at an end of a liquid sending channel 44a of the nozzle conduit 44. Furthermore, an O-ring 47 for keeping watertightness with respect to the conduit connector 43 is provided along the perimeter of the coupling section 48.

A resistor and a biasing member (elastic member) such as a spring (not shown) are provided inside the nozzle housing tube 45 and the nozzle conduit 44 is configured to be normally biased backward by the biasing member and moved forward when the resistor receives the resistance of the fluid that passes through the nozzle housing tube 45, by the liquid sending pressure against the biasing member.

The conduit connector 43 pivotably fits onto the coupling section 48, a sealing member 46 for keeping watertightness made of an elastic member such as rubber is provided at the opening of the end face communicating with the liquid sending channel 44a of the nozzle conduit 44 and a guide surface 43a which is a conical surface tapered backward is formed around the opening. Furthermore, a tapered surface 43b is also formed on the back end face of the conduit connector 43 so as not to interfere with the nozzle conduit 44 when pivoting.

The endoscope washing and disinfecting apparatus 1 of the present embodiment configured as shown above is controlled so that the nozzle unit 42 moves to, for example, three positions A to C as shown in FIG. 14 and is connected to the conduit base 101 of the endoscope 100 at the respective positions A to C.

The above described position A is the position of the endoscope 100 having one channel placed in the washing and disinfecting tank 4 corresponding to the conduit base 101, while the above described positions B and C are the positions of the endoscope 100 having two channels corresponding to two conduit bases 101 respectively.

At the position A, the conduit base 101 is located at a position on substantially the same axis as that of the conduit base 101, in other words, on the straight axial line on which the conduit connector 43 moves forward together with the nozzle conduit 44, and when a fluid is supplied, the conduit connector 43 moves forward and is thereby automatically connected to the conduit base 101.

Furthermore, at the position B, since the conduit base 101 is tilted such that the opening faces upward on the surface of the sheet, in the process in which the conduit connector 43 moves forward when the fluid is supplied, the outward flange 102 of the conduit base 101 comes into contact with the guide surface 43a, the conduit connector 43 pivots downward and is thereby automatically connected to the conduit base 101.

On the other hand, at the position C, since the conduit base 101 is tilted such that the opening faces downward on the surface of the sheet, in the process in which the conduit connector 43 moves forward when the fluid is supplied, the outward flange 102 of the conduit base 101 comes into contact with the guide surface 43a, the conduit connector 43 pivots upward and is thereby automatically connected to the conduit base 101.

When the conduit base 101 is connected to the conduit connector 43, since the sealing member 46 comes into close contact with the surface of the outward flange 102, the fluid such as washing fluid is supplied into the channel of the endoscope 100 via the conduit base 101 with substantially no leakage. Furthermore, the endoscope washing and disinfecting apparatus 1 washes and disinfects the inside of the two channels of the endoscope 100 by alternately moving the nozzle unit 42 between the positions B and C.

As described above, the endoscope washing and disinfecting apparatus 1 of the present embodiment can move one nozzle unit 42 and automatically attach/detach the nozzle unit 42 to/from the conduit base 101 according to the number of channels (here, cases with one and two channels are illustrated) depending on the type of the endoscope 100. Therefore, the endoscope washing and disinfecting apparatus 1 is configured so as to eliminate the necessity for providing the nozzle units 42 corresponding to the position of attachment/detachment to/from the conduit base 101 of the endoscope 100 having one channel and the positions of attachment/detachment to/from the conduit base 101 of the endoscope 100 having a plurality of channels respectively, can thereby reduce cost and prevent the size of the apparatus from increasing.

Furthermore, even if the conduit base 101 has a predetermined angle θ and is tilted in different directions, the endoscope washing and disinfecting apparatus 1 can make a connection with each conduit base 101 by adopting a simple configuration such as the nozzle unit 42 and causing the conduit connector 43 to rotate according to the tilting of each conduit base 101.

The rest of the configuration and operations of the endoscope washing and disinfecting apparatus 1 of the present embodiment are the same as those of the first embodiment, and therefore explanations thereof will be omitted.

The conduit connection structure of the nozzle unit 42 may also be like the configuration shown in FIG. 15 and FIG. 16.

More specifically, as shown in FIG. 15, the nozzle unit 42 here is provided with an O-ring 29 for keeping watertightness on an end face formed into a recessed spherical shape and a holding tube 49 is engaged so that a quasi-spherical conduit connector 27 is loosely fitted to the end of the nozzle conduit 44 of the nozzle unit 42. The distal end portion of the holding tube 49 is formed into a curved surface along the surface of the conduit connector 27.

A guide surface 27a is formed around the front opening of the quasi-spherical conduit connector 27 and a sealing member 46 is provided at the opening. Furthermore, a step 27b which is slightly diagonally notched backward and a tapered surface 27c whose rear opening spreads in a circumferential direction are formed around the rear part of the conduit connector 27. Furthermore, a spring 28 for biasing the conduit connector 27 forward is disposed inside the holding tube 49.

As shown in FIG. 16, when, for example, the nozzle unit 42 configured as shown above moves forward and joins the conduit base 101 of the endoscope 100 which is tilted downward on the surface of the sheet, the conduit connector 27 pivots upward with the surface of the outward flange 102 of the conduit base 101 contacting the guide surface 27a. At the same time as this, when the nozzle conduit 44 moves forward (in the direction indicated by an arrow F in the figure), the conduit connector 27 inside the holding tube 49 is pushed backward (in the direction indicated by an arrow B in the figure) against the biasing force of the spring 28.

The back outer surface of the conduit connector 27 then comes into close contact with the O-rings 29 provided on the surface of the nozzle conduit 44. That is, the nozzle unit 42 is connected to the conduit base 101 in a quasi-watertight manner by the sealing member 46 provided at the front opening of the conduit connector 27 coming into close contact with the surface of the outward flange 102 of the conduit base 101 and the back outer surface of the conduit connector 27 coming into close contact with the O-ring 29 provided on the surface of the nozzle conduit 44.

In addition to effects similar to those described above, the nozzle unit 42 in such a configuration still functions, even when the area of the guide surface 27a to suit the orientation of the conduit base 101 is reduced compared to the conduit connector 43 in FIG. 12 to FIG. 14, and therefore it is possible to reduce the size of the conduit connector 43.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A washing tube for supplying a washing and disinfecting fluid to an endoscope conduit of an endoscope placed in an endoscope washing and disinfecting apparatus, comprising:
    a tube body, one end of which is connected to a fluid supply section of the endoscope washing and disinfecting apparatus, for sending the fluid;
    a connector section disposed at the other end of the tube body and loosely fitted to a base of the endoscope conduit in a detachable manner;
    a sealing member that is provided inside the connector section, and comes into close contact with the base and keeps the base and the connector section connected in a watertight manner;
    an annular member provided with the sealing member, including a resisting surface for receiving a liquid sending pressure of the fluid formed on a back end face of the annular member;
    a valve body that includes the sealing member and the annular member and moves forward by a liquid sending pressure of the supplied fluid;
    a biasing member provided inside the connector section for biasing the valve body backward;
    a cylindrical section loosely inserted into a hole of the annular member of the valve body;
    a plurality of blades radially extending around a back perimeter of the cylindrical section;
    a plurality of holes formed at both ends of the cylindrical section to allow the fluid to flow into the cylindrical section; and
    a tubular body including the cylindrical section, the plurality of blades and the plurality of holes,
    wherein the plurality of blades move forward under a liquid sending pressure of the fluid, the cylindrical section is inserted into the base of the endoscope conduit and the fluid flows into the plurality of holes and the fluid is thereby supplied into the endoscope conduit via the cylindrical section.

2. An endoscope washing and disinfecting apparatus that automatically washes and disinfects an endoscope placed in a washing and disinfecting tank and detects conduit clogging of an endoscope conduit of the endoscope, comprising:
    a tube body, one end of which is connected to a fluid supply section, for sending the fluid;
    a connector section disposed at the other end of the tube body and loosely fitted to a base of the endoscope conduit in a detachable manner;
    a sealing member that is provided inside the connector section, and comes into close contact with the base and keeps the base and the connector section connected in a watertight manner;
    an annular member provided with the sealing member, including a resisting surface for receiving a liquid sending pressure of the fluid formed on a back end face of the annular member;
    a valve body that includes the sealing member and the annular member and moves forward by a liquid sending pressure of the supplied fluid;
    a biasing member provided inside the connector section for biasing the valve body backward;
    a cylindrical section loosely inserted into a hole of the annular member of the valve body;
    a plurality of blades radially extending around a back perimeter of the cylindrical section;
    a plurality of holes formed at both ends of the cylindrical section to allow the fluid to flow into the cylindrical section; and
    a tubular body including the cylindrical section, the plurality of blades and the plurality of holes,
    wherein the valve body is constructed so as to supply a predetermined flow rate of the fluid to the connector section from the fluid supply section via the tube body so as to obtain a predetermined liquid sending pressure under which the sealing member moves forward up to a position where the sealing member comes into close contact with the base against a biasing force of the biasing member and keeps watertightness with the connector section, and
    wherein the plurality of blades move forward under a liquid sending pressure of the fluid, the cylindrical section is inserted into the base of the endoscope conduit and the fluid flows into the plurality of holes and the fluid is thereby supplied into the endoscope conduit via the cylindrical section.

3. The endoscope washing and disinfecting apparatus according to claim 2, wherein the endoscope washing and disinfecting apparatus is constructed so as to supply a flow rate of the fluid from the fluid supply section to the connector section via the tube body so as to obtain a liquid sending pressure smaller than the predetermined liquid sending pressure so that a biasing force of the biasing member becomes greater, allows the fluid to flow over an outer surface of the base which is loosely fitted to the connector section and performs washing and disinfection.

* * * * *